(12) United States Patent
Dettmann et al.

(10) Patent No.: US 10,856,767 B2
(45) Date of Patent: Dec. 8, 2020

(54) 300 MHZ TO 3 THZ ELECTROMAGNETIC WAVE SENSOR FOR DETERMINING AN INTERSTITIAL FLUID PARAMETER IN VIVO

(71) Applicant: Infineon Technologies AG, Neubiberg (DE)

(72) Inventors: Wolfgang Dettmann, Schliersee (DE); Herbert Roedig, Riemerling (DE); Georg Schmidt, Gräfelfing (DE)

(73) Assignee: Infineon Technologies AG, Neubiberg (DE)

( * ) Notice: Subject to any disclaimer, the term of this patent is extended or adjusted under 35 U.S.C. 154(b) by 628 days.

(21) Appl. No.: 15/324,306

(22) PCT Filed: Jul. 7, 2015

(86) PCT No.: PCT/EP2015/001389
§ 371 (c)(1),
(2) Date: Jan. 6, 2017

(87) PCT Pub. No.: WO2016/005050
PCT Pub. Date: Jan. 14, 2016

(65) Prior Publication Data
US 2017/0181658 A1   Jun. 29, 2017

(30) Foreign Application Priority Data

Jul. 8, 2014  (DE) .................. 10 2014 109 549

(51) Int. Cl.
*A61B 5/145* (2006.01)
*A61B 5/05* (2006.01)
*A61B 5/00* (2006.01)

(52) U.S. Cl.
CPC .......... *A61B 5/0507* (2013.01); *A61B 5/0031* (2013.01); *A61B 5/1451* (2013.01);
(Continued)

(58) Field of Classification Search
CPC . A61B 5/0507; A61B 5/0031; A61B 5/14503; A61B 5/1451; A61B 5/14532;
(Continued)

(56) References Cited

U.S. PATENT DOCUMENTS 6,723,048 B2 * 4/2004 Fuller ...................... A61B 5/05
   335/302
7,122,012 B2 * 10/2006 Bouton ..................... A61B 5/05
   600/587

(Continued)

FOREIGN PATENT DOCUMENTS

| DE | 102011080192 A1 | 2/2013 |
| WO | 2009031149 A2 | 3/2009 |
| WO | 2013164827 A2 | 11/2013 |

*Primary Examiner* — Navin Natnithithadha
(74) *Attorney, Agent, or Firm* — Murphy, Bilak & Homiller, PLLC

(57) ABSTRACT

An electromagnetic wave sensor for determining an interstitial fluid parameter in vivo comprises an implantable housing, and a sensor component hermetically encapsulated within the implantable housing. The sensor component comprises an electromagnetic wave transmitter unit configured to emit an electromagnetic wave signal in a frequency range between 300 MHz and 3 THz penetrating the implantable housing and penetrating an interstitial fluid probe volume, an electromagnetic wave receiver unit configured to receive the electromagnetic wave signal modified by the interstitial fluid probe volume, and a transceiver unit configured to transmit radio frequency signals related to the electromagnetic wave signal modified by the interstitial fluid probe volume. A system for determining an interstitial fluid parameter in vivo comprises the electromagnetic wave sensor and an external reader.

21 Claims, 9 Drawing Sheets

(52) U.S. Cl.
CPC ...... *A61B 5/14503* (2013.01); *A61B 5/14532* (2013.01); *A61B 5/6861* (2013.01); *A61B 2560/0219* (2013.01); *A61B 2562/0271* (2013.01); *A61B 2562/143* (2013.01); *A61B 2562/166* (2013.01)

(58) Field of Classification Search
CPC .......... A61B 5/6861; A61B 2560/0219; A61B 2562/0271; A61B 2562/143; A61B 2562/166
USPC ................................ 600/309, 365, 407, 409
See application file for complete search history.

(56) References Cited

U.S. PATENT DOCUMENTS

| | | | |
|---|---|---|---|
| 7,184,824 B2* | 2/2007 | Hashimshony | A61B 5/0507 600/547 |
| 8,368,402 B2* | 2/2013 | Lee | G01N 24/08 324/318 |
| 8,836,334 B2* | 9/2014 | Lee | G01N 24/08 324/318 |
| 9,339,189 B2 | 5/2016 | Göhler et al. | |
| 2002/0128546 A1 | 9/2002 | Silver | |
| 2010/0072994 A1* | 3/2010 | Lee | G01N 24/08 324/307 |
| 2011/0160554 A1* | 6/2011 | Megej | A61B 5/0507 600/365 |
| 2011/0256024 A1 | 10/2011 | Cole et al. | |
| 2013/0060103 A1 | 3/2013 | Bergida et al. | |
| 2013/0144134 A1* | 6/2013 | Lee | G01N 24/08 600/309 |
| 2013/0289370 A1* | 10/2013 | Sun | A61B 5/14532 600/316 |
| 2014/0062717 A1 | 3/2014 | Mudumbai et al. | |
| 2015/0133763 A1* | 5/2015 | Saroka | A61B 5/6833 600/407 |
| 2018/0325431 A1* | 11/2018 | Guarin | A61B 5/1495 |

* cited by examiner

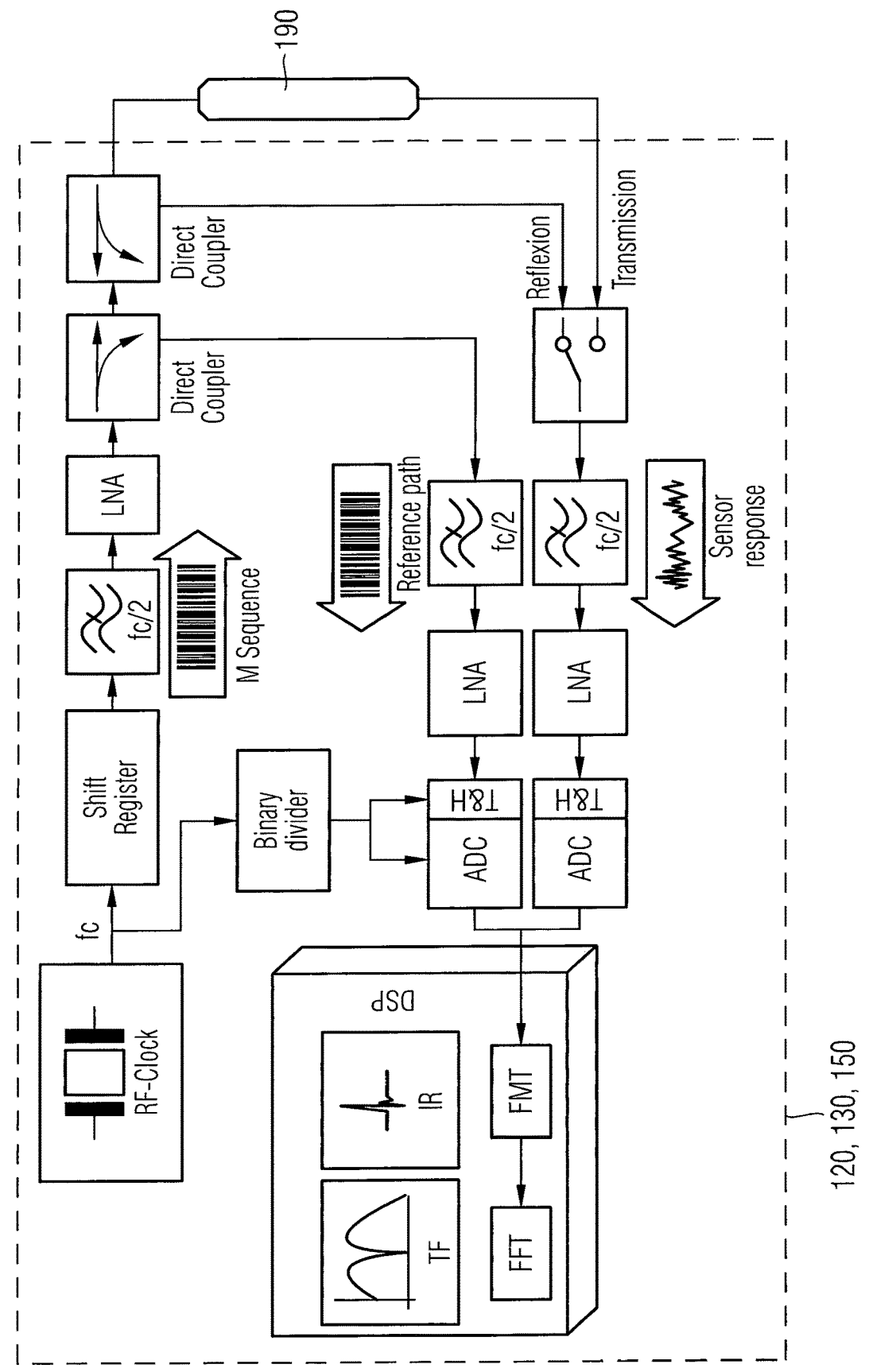

300 MHZ TO 3 THZ ELECTROMAGNETIC WAVE SENSOR FOR DETERMINING AN INTERSTITIAL FLUID PARAMETER IN VIVO

BACKGROUND

Blood picture parameters such as, for example, a concentration of a blood constituent, can be ascertained by taking blood invasively and analyzing the blood by means of standardized test strips. An electric resistance value of the blood can be detected using a blood sugar measuring instrument, which carries out a DC current resistance measurement for detecting an electric resistance value of a test strip. The resistance value can then be converted into a blood sugar concentration on the basis of a relationship, known per se, between a blood sugar concentration and a resistance value. A high detection accuracy may be achieved by providing each test strip with calibration data, for example with a reference resistance value or with a corresponding code, as a result of which variations of properties of the test strips can be compensated for.

Invasive methods is the necessity of taking blood and hence of injuring a patient. Moreover, continuous detection of a concentration of a blood constituent, for example to establish the diurnal variation curve thereof, is challenging. Furthermore, it is challenging to detect a time delay between food being taken and, for example, an increase in the blood sugar accurately by means of the invasive method.

Non-invasive measurement methods however may lead to different measurement results depending on different measurement environments at each measurement event.

It is an object of the present invention to provide a device for determining a body fluid parameter in vivo having an improved reliability and precision.

SUMMARY

This object is solved by the subject-matter of the independent claims. Further advantageous embodiments and refinements are defined in the respective sub-claims.

According to an embodiment of an electromagnetic wave sensor for determining an interstitial fluid parameter in vivo, the electromagnetic wave sensor comprises an implantable housing, and a sensor component hermetically encapsulated within the implantable housing. The sensor component further comprises an electromagnetic wave transmitter unit configured to emit an electromagnetic wave signal in a frequency range between 300 MHz and 3 THz penetrating the implantable housing and penetrating an interstitial fluid probe volume, and an electromagnetic wave receiver unit configured to receive the electromagnetic wave signal modified by the interstitial fluid probe volume. In addition, the sensor component comprises a transceiver unit configured to transmit radio frequency signals related to the electromagnetic wave signal modified by the interstitial fluid probe volume.

According to an embodiment of a system for determining an interstitial fluid parameter in vivo, the system comprises an electromagnetic wave sensor and an external reader. The electromagnetic wave sensor comprises an implantable housing, and a sensor component hermetically encapsulated within the implantable housing. The sensor component comprises an electromagnetic wave transmitter unit configured to emit an electromagnetic wave signal in a frequency range between 300 MHz and 3 THz penetrating the implantable housing and penetrating an interstitial fluid probe volume, an electromagnetic wave receiver unit configured to receive the emitted electromagnetic wave signal modified by the interstitial fluid probe volume, and a data transceiver unit configured to communicate with the external reader. The external reader is configured to transmit radio frequency energy powering the electromagnetic wave sensor and is further configured to receive radio frequency signals from the electromagnetic wave sensor related to the electromagnetic wave signal modified by the interstitial fluid probe volume.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description.

FIG. 7C is a schematic block diagram illustrating an ultra-wideband impedance spectrometer setup in a transmission and reflection mode of the electromagnetic wave sensor according to an embodiment.

DETAILED DESCRIPTION

In the following detailed description, reference is made to the accompanying drawings, which form a part hereof, and in which are shown by way of illustrations specific embodiments in which the invention may be practiced. It is to be understood that other embodiments may be utilized and structural or logical changes may be made without departing from the scope of the present invention. For example, features illustrated or described for one embodiment can be used on or in conjunction with other embodiments to yield yet a further embodiment. It is intended that the present invention includes such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", "an" and "the" are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s) adapted for signal transmission may be provided between the electrically coupled elements, for example resistors, resistive elements or elements that are controllable to temporarily provide a low-ohmic connection in a first state and a high-ohmic electric decoupling in a second state.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

Figure 1:
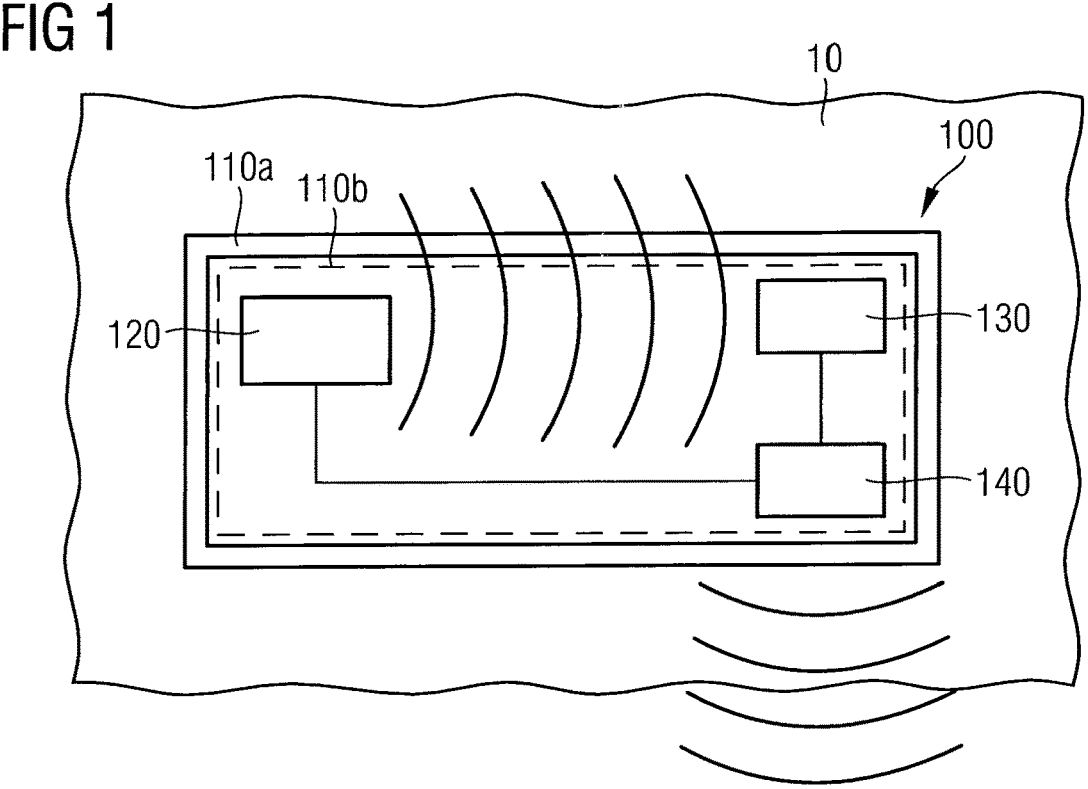
FIG. 1 is a schematic block diagram of an electromagnetic wave sensor according to an embodiment.

FIG. 1 is a schematic block diagram of an electromagnetic wave sensor 100 for determining an interstitial fluid parameter in vivo according to an embodiment. As shown in FIG. 1, the electromagnetic wave sensor 100 comprises an implantable housing 110a and a sensor component 110b hermetically encapsulated within the implantable housing 100a. The sensor component 110b comprises an electromagnetic wave transmitter unit 120 configured to emit an electromagnetic wave signal penetrating the implantable housing 110a and penetrating an interstitial fluid probe volume 10. The sensor component 110b further comprises an electromagnetic wave receiver unit 130 configured to receive the electromagnetic wave signal modified by the interstitial fluid probe volume 10. In addition, the sensor component 110b comprises a transceiver unit 140 configured to transmit radio frequency signals related to the electromagnetic wave signal modified by the interstitial fluid probe volume 10.

The interstitial probe volume 10 is that part of an interstitial fluid surrounding the implantable housing 110a, which is penetrated by the electromagnetic wave signal emitted by the electromagnetic wave transmitter unit 120 and which has an influence on the electromagnetic wave signal in such a way that the electromagnetic wave signal is modified. A modification of the electromagnetic wave signal may be an attenuation or phase change of the electromagnetic wave signal in dependence of the electromagnetic wave frequency, for example. The electromagnetic wave signal modified by the interstitial fluid probe volume 10 is then received by the electromagnetic wave receiver unit 140 after transmission or reflection, wherein the modification of the electromagnetic wave signal allows a measurement of the interstitial fluid parameter of the interstitial fluid probe volume 10.

Due to the implantation of the electromagnetic wave sensor 100 within a body in vivo, the electromagnetic wave sensor 100 is substantially fixed within the body. Thus, the measurement environment in vivo does not change subject to a composition of the interstitial fluid, leading to reproducible and reliable measurement results being not influenced by a change of other measurement parameters such as a varying position of bones or blood vessels.

Figure 2:
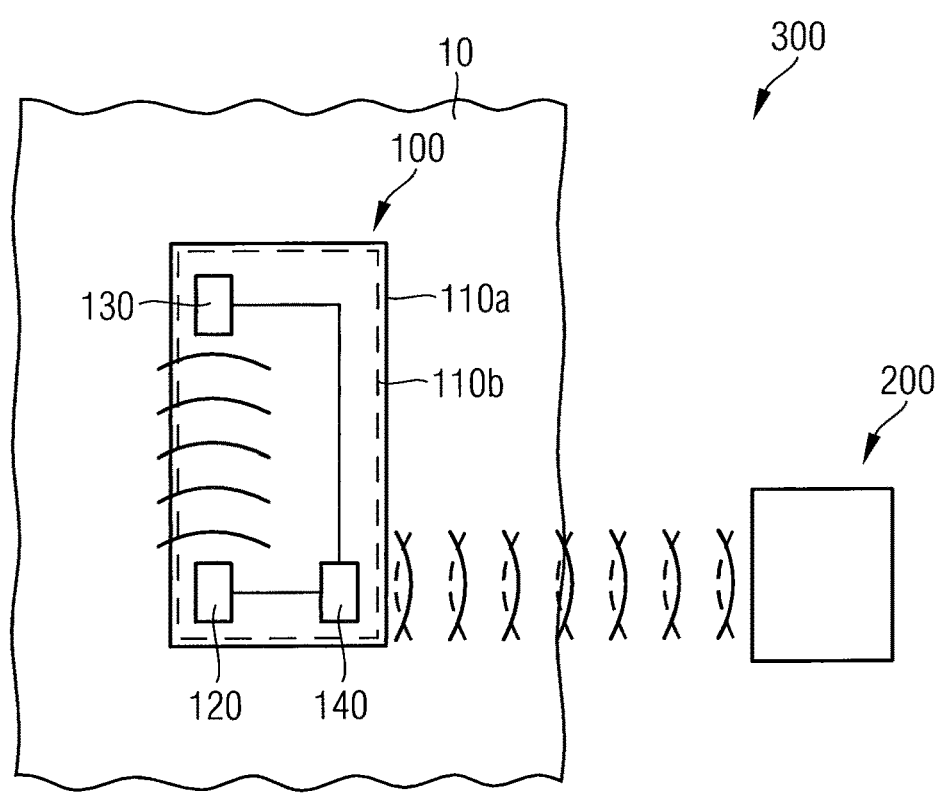
FIG. 2 is a schematic block diagram of a system for determining an interstitial fluid parameter in vivo according to an embodiment.

FIG. 2 is a schematic block diagram of a system 300 for determining an interstitial fluid parameter in vivo according to an embodiment. As can be seen from FIG. 2, the system 300 comprises the electromagnetic wave sensor 100 and an external reader 200. The electromagnetic wave sensor 100 comprises the implantable housing 110a and the sensor component 110b hermetically encapsulated within the implantable housing 110a. The sensor component 110b comprises the electromagnetic wave transmitter unit 120 configured to emit an electromagnetic wave signal penetrating the implantable housing 110a and penetrating the interstitial fluid probe volume 10, and the electromagnetic wave receiver unit 130 configured to receive the electromagnetic wave signal modified by the interstitial fluid probe volume 10. The sensor component 110b further comprises a data transceiver unit 140 configured to communicate with the external reader 200. In an embodiment, the external reader 200 may be configured to transmit radio frequency energy in a frequency range between 400 MHz and 1 GHz powering the electromagnetic wave sensor 100. In another embodiment, the external reader 200 may be configured to power the electromagnetic wave sensor 100 by inductive magnetic coupling in a frequency range between 100 kHz and 20 MHz. The external reader 200 is further configured to receive radio frequency signals from the electromagnetic wave sensor 100 related to the electromagnetic wave signal modified by the interstitial fluid probe volume 10.

Figure 3:
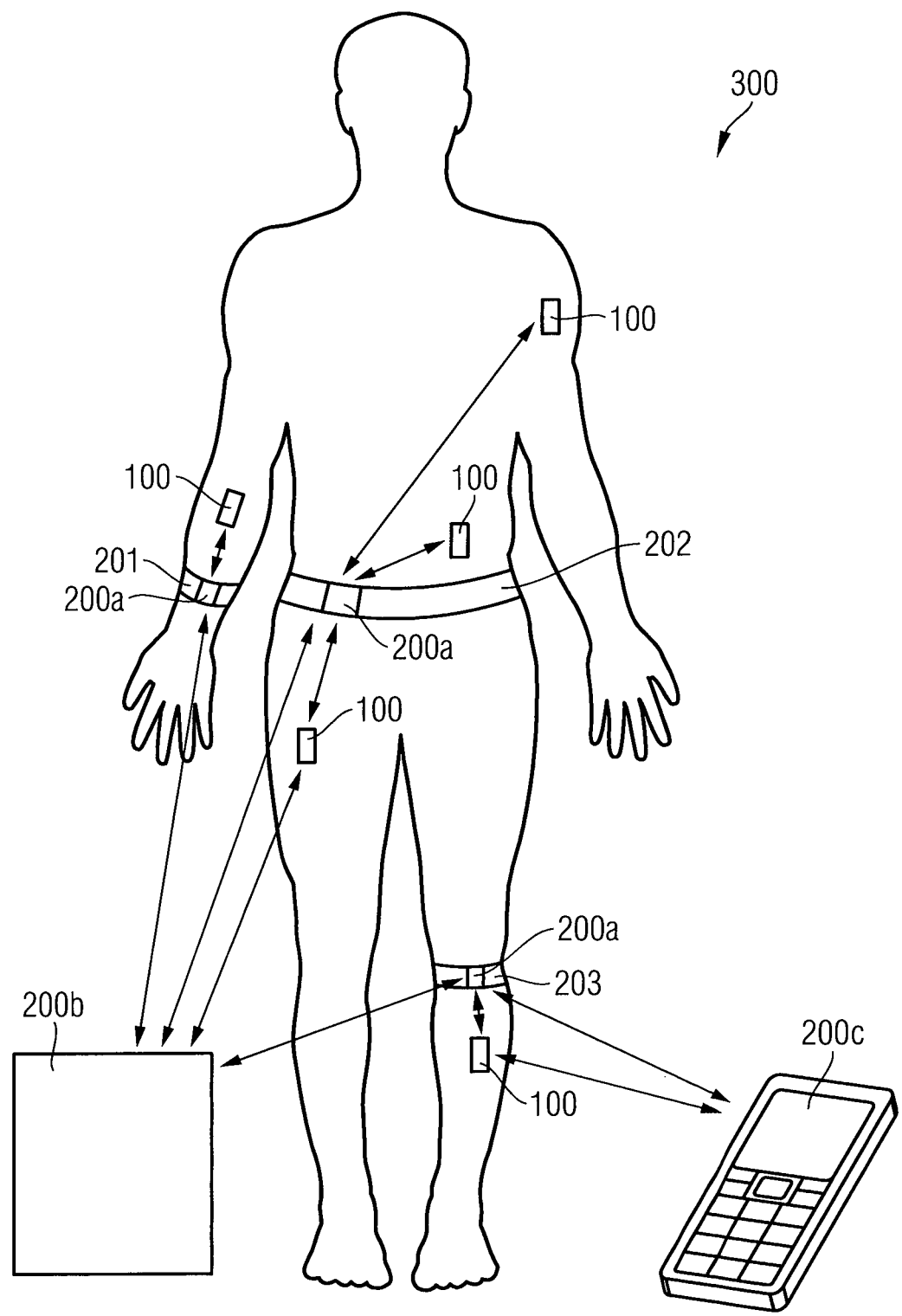
FIG. 3 is a schematic diagram illustrating various employments of the electromagnetic wave sensor within a human body in combination with an external reader according to different embodiments.

FIG. 3 is a schematic diagram illustrating various employments of the electromagnetic wave sensor 100 within a human body in combination with an external reader 200.

The electromagnetic wave sensor 100 may be implanted within a dermal tissue of a human body in a region of the body, in which the electromagnetic wave sensor 100 does not interfere with any movements of the human body. The electromagnetic wave sensor 100 may also be implanted within a fat tissue of a human body, e.g. in a hip region of the body. The size of the electromagnetic wave sensor 100 is substantially limited by the wavelength of the emitted electromagnetic wave signal. Taking an electromagnetic wave frequency for probing the interstitial fluid probe volume 10 of 3 GHz to 30 GHz (Super High Frequency region), the freespace wavelength is in the order of 10 cm to 1 cm. In case of choosing electromagnetic waves in a frequency range of 30 GHz to 300 GHz (Extremely Frequency region) the freespace wavelength is in a range of 1 cm to 1 mm. The electromagnetic wave frequency may even be higher in a range of 300 GHz to 3 THz, leading to a freespace wavelength in a sub-millimeter-range. Thus, the higher the probing electromagnetic wave signal frequency, the smaller the electromagnetic wave sensor 100 can be designed. The external reader 200 may be a mobile device 200a being fixed to an armband 201, a belt 202 in a hip region or a belt 203 in a leg region. In case of using a mobile device 200a in combination with the electromagnetic wave sensor 100, all electronic components having a high space consumption may be integrated within the mobile device 200a, to reduce the size of the electromagnetic wave sensor 100. For example, the data processing may be achieved by the mobile device 200a, wherein the electromagnetic wave sensor 100 transmits only raw data related to the electromagnetic wave signal modified by the interstitial fluid probe volume 10. The external reader 200 may also be a device 200b such as a personal computer, which is stationary, for example at a home place, to communicate with the mobile device 200a or directly with the electromagnetic wave sensor 100, a tablet personal computer, or a bedside device. Furthermore, the external reader 200 may be a cellular phone 200c, which communicates with the mobile device 200a or directly with the electromagnetic wave sensor 100. In case the cellular phone 200c directly communicates with the electromagnetic wave sensor 100, the data transceiver unit 140 of the electromagnetic wave sensor 100 has to be configured to transfer data to the cellular phone 200c using a standard protocol implemented within the cellular phone 200c.

Figure 4:
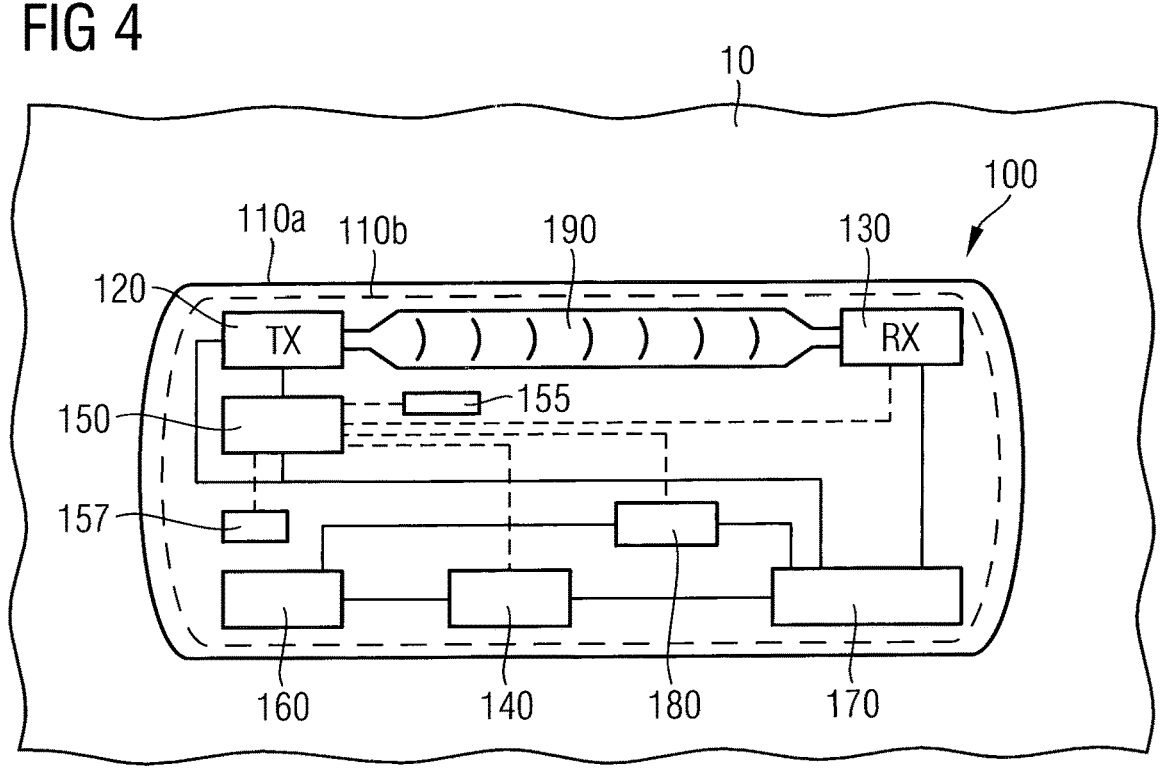
FIG. 4 is a schematic block diagram of an electromagnetic wave sensor according to an embodiment.

FIG. 4 is a schematic block diagram of an electromagnetic wave sensor 100 for determining an interstitial fluid parameter in vivo according to an embodiment.

As shown in FIG. 4, the electromagnetic wave sensor 100 comprises the implantable housing 110a and the sensor component 110b hermetically encapsulated within the implantable housing 110a. The sensor component 110b may comprise all electronic components of the electromagnetic wave sensor 100, wherein these components are encased in a high-integrity hermetic implantable housing 110a. The implantable housing 110a may be made of a non-metallic biocompatible material which is suitable for long-term implantation in a human or other animal. The material of the implantable housing 110a for encapsulating the sensor component 110b may comprise ceramics, silicone on parylene coating and glass encapsulation. The implantable housing 110a may be further fashioned from one or more of a variety of biocompatible materials suitable for long-term implantation in a human or other animal. Such materials include glass, plastics, synthetic carbon-or silicon-based materials, fluoropolymers such as polytetrafluoroethylene (PTFE), perfluoroalkoxy alkanes (PFA) or ethylene tetrafluoroethylene (ETFE).

The implantable housing 110a may be designed to be substantially fluid and gas impermeable to hermetically encapsulate the sensor component 110b. As a result, a contactless measurement of an interstitial fluid parameter is possible, wherein the tissue surrounding the implantable housing 110a is in direct contact with the biocompatible implantable housing 110a only, and is not in direct contact with the sensor component 110b enclosed within the implantable housing 110a.

The implantable housing 110a may further comprise means for fixing the implantable housing 110a within a surrounding subcutaneous or other tissue of a human or animal. Thus, the implantable housing 110a of the electromagnetic wave sensor 100 may be fixed within the surrounding tissue, e.g. by saturating or by hook means or by a specific form of the housing 110a such as a butterfly wing form, ensuring a constant measurement environment resulting in reliable measurement results of the electromagnetic wave sensor 100 determining the interstitial fluid parameter in vivo.

The interstitial fluid parameter of the interstitial fluid probe volume 10 surrounding the electromagnetic wave sensor 100 may be a glucose concentration within the interstitial fluid probe volume 10. It has been found that a glucose concentration within an interstitial fluid reflects the blood sugar concentration within a delay time of 10 to 20 minutes. Thus, a blood sugar concentration may be determined by measuring the glucose concentration within the interstitial fluid probe volume 10. However, the interstitial fluid parameter may be any parameter of the interstitial fluid probe volume 10 which has an impact on an electromagnetic wave signal penetrating the interstitial fluid probe volume 10, and which may have a medical importance.

As can be seen from FIG. 4, the sensor component 110b comprises the electromagnetic wave transmitter unit 120 (indicated as TX) configured to emit an electromagnetic wave signal penetrating the implantable housing 110a and penetrating an interstitial fluid probe volume 10, the electromagnetic wave receiver unit 130 (indicated as RX) configured to receive the electromagnetic wave signal modified by the interstitial fluid probe volume 10, and the transceiver unit 140 configured to transmit radio frequency signals related to the electromagnetic wave signal modified by the interstitial fluid probe volume 10. The sensor component 110b may further comprise a processor unit 150, which is connected via a data line (indicated by the dotted line) with the electromagnetic wave transmitter unit 120 and the electromagnetic wave receiver unit 130. The processor unit 150 is configured to process parameters of the emitted electromagnetic wave signal, which are received from the electromagnetic wave transmitter unit 120 via the data line, and to process parameters of the electromagnetic wave signal modified by the interstitial fluid probe volume 10, which are received from the electromagnetic wave receiver unit 130 via the data line. The processor unit 150 may be further connected via a data line to a memory unit 155, which is configured to store measurement raw data or processed data from the processor unit 150. The processor unit 150 is further connected via a data line to the transceiver unit 140, to provide the transceiver unit 140 with processed data to be transmitted to an external reader 200 via an antenna unit 160. The sensor units 120 to 150 are powered via power lines (indicated by a continuous line) from a energy storage unit 170. The energy storage unit 170 may be charged by an energy harvesting unit 180, which may be connected to the antenna unit 160, thus using the antenna unit 160 in common with the transceiver unit 140. Furthermore, according to an embodiment, the sensor component 110b may comprise a temperature sensor 157 for measuring the temperature of the surrounding interstitial fluid probe volume 10. The temperature data is transmitted to the processor unit 150, to consider a temperature variation of the interstitial fluid probe volume 10 in the analysis of the interstitial fluid parameter. Although a possible temperature change of a human is low in view of the absolute temperature (310 K±5 K), it has been found that the temperature of the interstitial fluid probe volume 10 may have a non-negligible influence on the transmission or reflection spectra of the electromagnetic waves in the microwave range, millimetre wave range or sub-millimetre wave range, which will be discussed below with regard to FIGS. 6A and 6B.

Figure 5A:
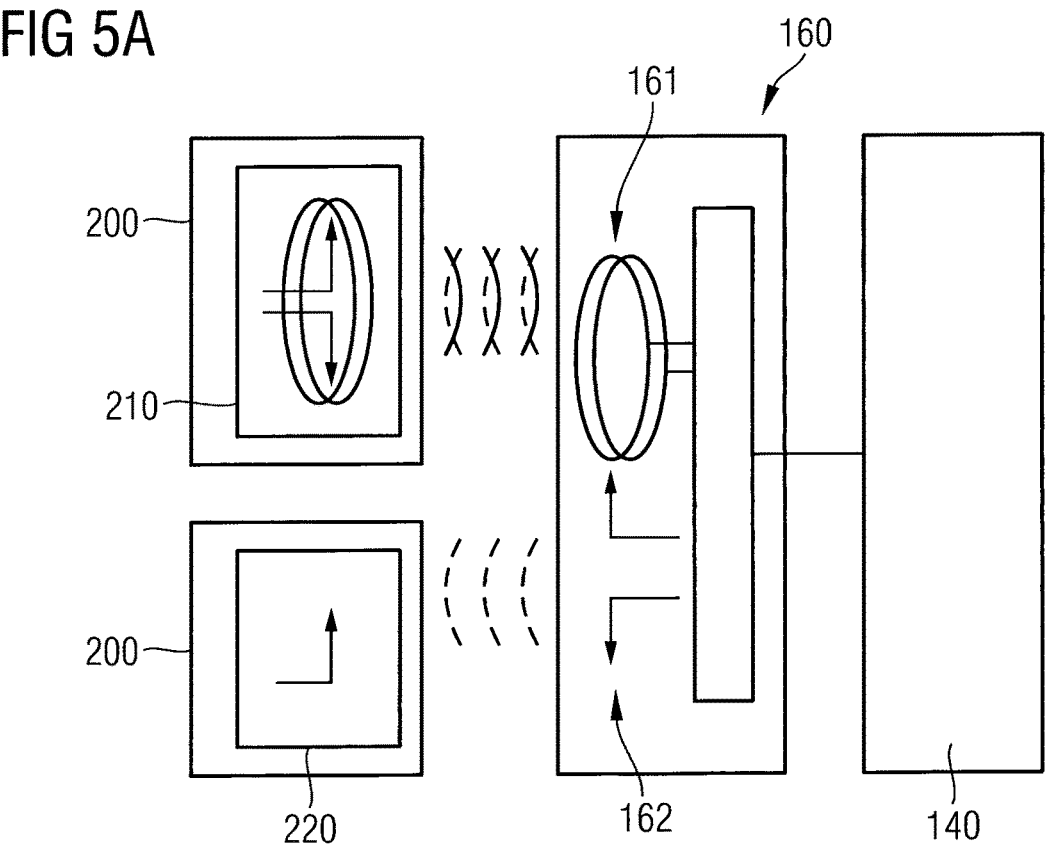
FIG. 5A is a schematic block diagram of an antenna unit of the electromagnetic wave sensor in communication with an external reader according to an embodiment.

In the following, the above units shall be described in more detail. FIG. 5A is a schematic block diagram of the antenna unit 160 and a transceiver unit 140 communicating with an external reader 200. The wireless communication of the transceiver unit 140 with the external reader 200 may include a plurality of different wireless communication protocols and various communication frequency bands. The transceiver unit 140 may also receive update programs from the external reader to adapt a communication procedure with the external reader. The update programs may also be provided for updating an operating system of the processor unit 150. In the embodiment shown in FIG. 5A, the antenna unit 160 may comprise at least one of a radio frequency identification (RFID)/near, field communication (NFC) antenna 161 communicating with the respective antenna 210 within the external reader 200 and an RFID/ultra-high frequency (UHF) antenna 162 communicating with the respective antenna 220 within the external reader 200.

RFID devices operate at different radio frequency ranges, e.g. low frequency (LF) at about 28 to 135 kHz, high frequency (HF) at about 13.56 MHz, and ultra-high frequency (UHF) at 860 to 960 MHz. Each frequency range has unique characteristic in terms of RFID performance.

NFC is a short range technology that enables two devices to communicate when they are brought into actual touching distance. NFC enables sharing power and data using magnetic field induction at 13.56 MHz (HF) band, at short range, supporting varying data rates from 106 kbps, 212 kbps to 424 kbps. A key feature of NFC is that is allows two devices to interconnect. In reader/writer mode, an NFC tag is a passive device that stores data that can be read by an NFC enable device. In peer-to-peer mode, two NFC devices can exchange data. Bluetooth or WiFi link set up parameters can be shared using NFC and data such as virtual business cards or digital photos can be exchanged. In card emulation mode, the NFC device itself acts as an NFC tag, appearing to an external interrogator as a traditional contact less smart card. These NFC standards are acknowledged by major standardisation bodies and based on ISO/IEC 18092.

Passive UHF systems use propagation coupling, where an interrogator antenna emits electromagnetic energy radio frequency waves and the RFID tag receives the energy from the interrogator antenna, and the integrated circuit uses the energy to change the load on the antenna and reflect back an altered signal that is then demodulated. For the LF and HF RFID systems using interactive coupling, the range of the interrogator field is small (0.2 to 80 cm) and can be relatively easily controlled. UHF systems that use propagation coupling are harder to control, because energy is sent over long distances. The radio waves can reflect on hard surfaces and reach tags that are not in the normal range. LF and HF systems perform better than UHF systems around metal and water. The radio waves do reflect off metal and cause false reads, and they are better able to penetrate water. UHF radio waves are attenuated by water.

In addition, communication may be performed via any one of an Industrial, Scientific and Medical (ISM) Band, which operates in a frequency range between 6.765 MHz to 246 GHz and has bandwidths of up to 2 GHz.

Figure 5B:
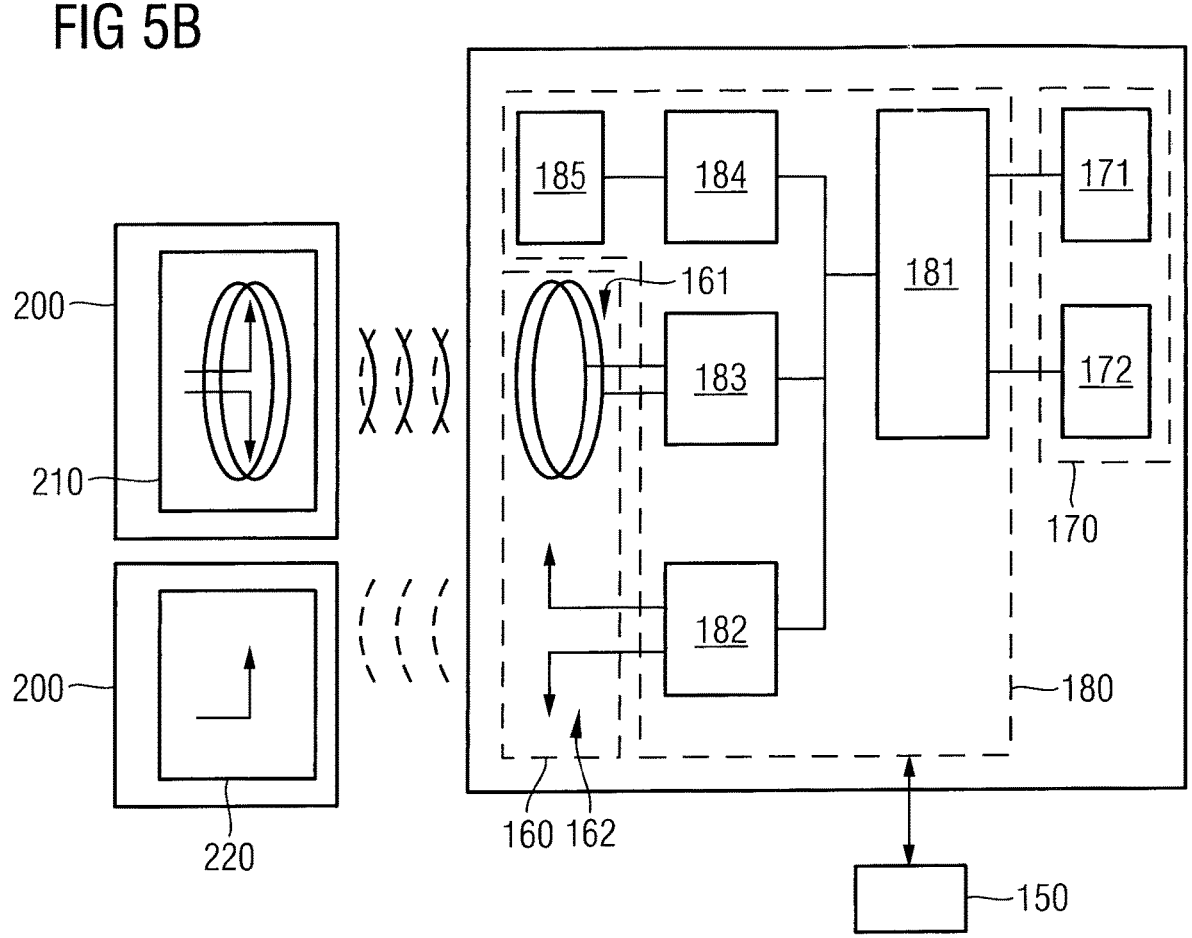
FIG. 5B is a schematic block diagram of an antenna unit, an energy storage unit, an energy harvesting unit, and a processor of the electromagnetic wave sensor being in communication with an external reader according to an embodiment.

FIG. 5B is a schematic block diagram showing the energy harvesting unit 180 being connected to the antenna unit 160, to harvest energy from an external power source, e.g. the external reader 200, for charging an energy storage unit 170. The energy harvesting unit 180 may be controlled by the processor unit 150. The energy harvesting unit 180 comprises a power management unit 181, which is connected to a HF power converter 183 for converting power from the RFID/NFC antenna 161 and is further connected to an UHF power converter 182, which is connected to the RFID/UHF antenna 162 of the antenna unit 160.

Energy may be harvested through a dedicated radio frequency source, and energy may be harvested from ambient radio frequency. The HF power converter 183 connected to the RFID/NFC antenna 161 is able to harvest energy from different external readers 200 such as smartphones or RFID readers to power data transmission. The UHF power converter 182 connected to the RFID/UHF antenna 162 is able to harvest ambient radio frequency energy from existing external energy sources like TV signal, WiFi/WiMAX, GSM and others. Furthermore, the energy harvesting unit 180 may comprise a DC to DC converter 184 connected to a thermal or piezoelectric harvester 185. Herein, kinetic energy may be harvested to obtain energy from human motion.

The energy storage unit 170 may comprise a chargeable storage device 171. Herein, a silicon-based rechargeable lithium battery may be used. As silicon has highest lithium ion storage capacity/volume, even a very tiny-sized battery (A<1 mm$^2$) may provide storage capacity in the order of up to 250 to 500 µAh, which is sufficient for various applications. The energy storage unit 170 may further comprise a capacitor 172. Herein, printed energy storage devices or printed supercapacitors may be used.

As shown in FIG. 4, the sensor component 110b may further comprise a waveguide unit 190 coupled to the electromagnetic wave transmitter unit 120 and the electromagnetic wave receiver unit 130, wherein the waveguide unit 190 is arranged within the implantable housing 110a such that a fringe field of the electromagnetic wave signal of the waveguide unit 190 penetrates the implantable housing 110a and the interstitial fluid probe volume 10. As shown in the embodiment of FIG. 4, the electromagnetic wave transmitter unit 120 and the electromagnetic wave receiver unit 130 may be arranged at opposite ends of the waveguide unit 190. Thus, a forward transmission factor may be determined. However, it is also possible to arrange the electromagnetic wave transceiver unit 120 and the electromagnetic wave receiver unit 130 at a same end of the waveguide unit 190, as shown, for example in FIG. 7B or 7C. According to the embodiment of FIG. 7B, the electromagnetic wave transmitter unit 120 may be embodied as an electromagnetic wave transceiver unit, wherein the electromagnetic wave receiver unit 130 is not arranged at the opposite end of the waveguide unit 190. However, as can be seen from FIG. 7C, the electromagnetic wave receiver unit 130 may be arranged at the opposite end of the waveguide unit 190 in addition to providing an electromagnetic wave transceiver unit at the end opposite to the electromagnetic wave receiver unit 130. In the measurement arrangement of FIGS. 7B and 7C, an input reflection factor may be determined. The electromagnetic wave transmitter unit 120 (as transmitter or transceiver) and the electromagnetic wave receiver unit 130 may also be embodied as one unit, for example in an integrated circuit on a monolithic chip.

The length of the waveguide unit 190 may be quarter or half of a maximum guided wavelength of the electromagnetic wave signal emitted by the electromagnetic wave transceiver unit 120 to ensure an optimized emission characteristics of the waveguide unit 190. The term guided wavelength will be discussed below.

Figure 5C:
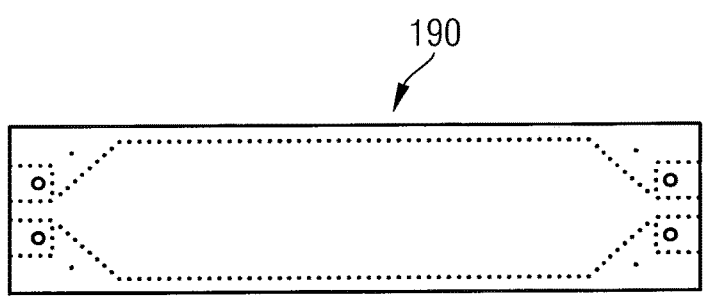
FIG. 5C is a schematic plan view of a waveguide unit of the electromagnetic wave sensor according to an embodiment.
Figure 5D:
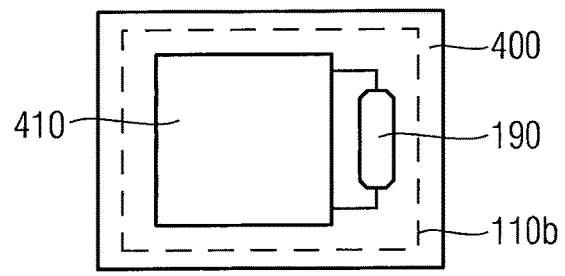
FIG. 5D is a schematic plan view of sensor component being integrated in a monolithic circuit according to an embodiment.

FIG. 5C is a plan view of a waveguide unit 190, wherein the waveguide unit 190 is embodied as a microstrip line. As shown in FIG. 5D, the waveguide unit 190 may also be arranged on a chip surface in case the sensor component 110*b* is integrated in a monolithic circuit, e.g. of a silicon chip.

Figure 5E:
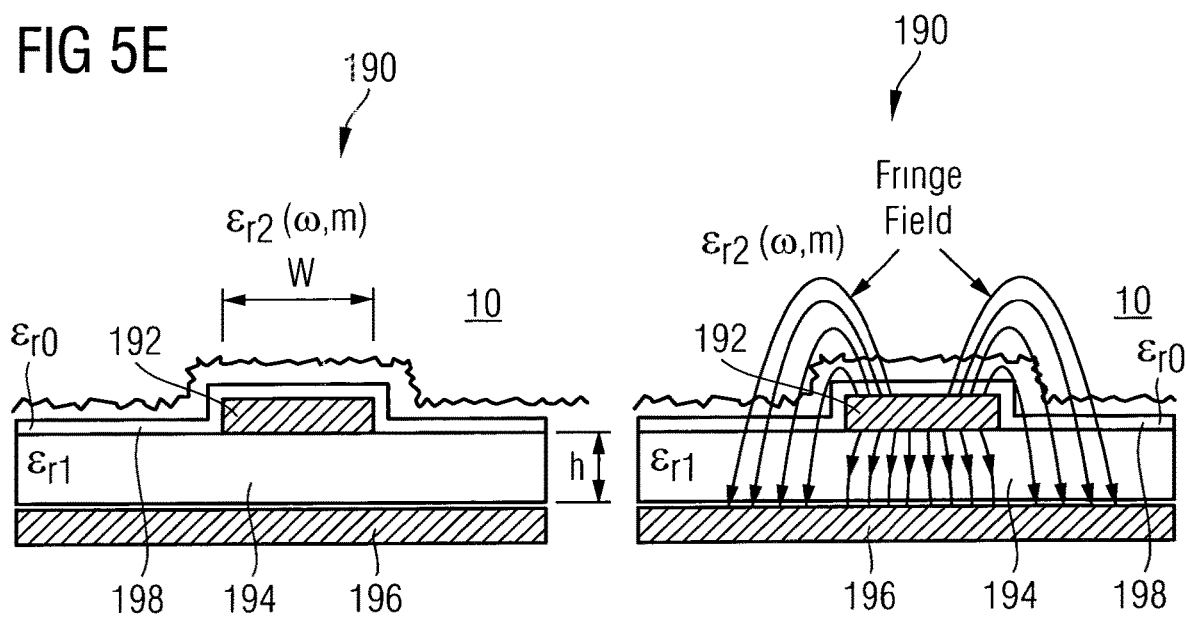
FIG. 5E is a schematic cross-sectional view of a portion of a waveguide unit of the electromagnetic wave sensor according to an embodiment.

The principle of the emission of a fringe field of the waveguide unit 190 is illustrated in FIG. 5E. In the waveguide unit 190, the electric and magnetic fields are only partially contained within the waveguide unit 190, because the conductor is not wholly shielded. Although the term "waveguide" is used, it should be emphasized that this term is not to be understood as a perfect waveguide, in which the electromagnetic field is fully shielded but as a dielectrically loaded waveguide or transmission line, in which a fringe field is extended into the interstitial fluid to be probed by the same. The waveguide unit shown in FIG. 5E comprises a signal guiding line 192, e.g. of a metal such as copper, provided on a dielectric substrate 194 having a permittivity $\in_{r1}$ and made of a ceramic or plastic material, for example. On a surface of the substrate 194 opposite to the signal guiding line 192, a conductive layer 196 is provided, acting as ground for the signal guiding line 194. A passivation layer 198 having a permittivity $\in_{r0}$ may further be provided, covering the dielectric substrate 194 and the signal guiding line 192. In an embodiment, the part of the implantable housing 110*a*, in which the waveguide unit 190 is provided, may be represented by the passivation layer 198, which hermetically encapsulates the sensor component 110*b* together with the remaining parts of the implantable housing 110*a*. The implantable housing 110*a* may, however be formed of one material only, wherein the electromagnetic waves penetrate this material. In an embodiment, the passivation layer 198 may be a passivation layer of a chip surface of a monolithic circuit as shown in FIG. 5D. The penetration depth of the electromagnetic waves into the interstitial fluid probe volume 10 may be in a range of 1 mm to 10 mm, depending on the frequency of the probing electromagnetic waves.

If the waveguide unit 190 is brought in contact with a tissue containing the interstitial fluid probe volume 10, the fringing field outside the substrate may interact with the tissue. The fringing field can penetrate the implantable housing 110*a* and the interstitial fluid probe volume 10 and on this way can interact with the interstitial fluid probe volume 10 having a permittivity $\epsilon_{r2}$. The interaction between the tissue and the waveguide unit 190 can be modelled through the effective permittivity on the waveguide unit 190 as shown in FIGS. 5C and 5D, wherein the permittivity of the thin passivation layer 198 has been be neglected.

$$\varepsilon_{\mathit{eff}} = \varepsilon_{r1} q_1 + \varepsilon_{r2} \frac{(1 - q_1)^2}{\varepsilon_{r2}(1 - q_1 - q_2) + q_2} \quad (1)$$

In formula (1), $q_1$ and $q_2$ are the ratios of the electromagnetic field energy in the dielectric substrate 194 having the permittivity $\epsilon_{r1}$ and the interstitial fluid probe volume 10 having the permittivity $\in_{r2}$, respectively. $q_1$ and $q_2$ are values in a range between 0 and 1. The wavelength of the electromagnetic wave guided in the waveguide unit 190 is indicated as guided wavelength $\lambda_g$, wherein the corresponding wavelength in vacuum is indicated as freespace wavelength $\lambda_0$. The relation between $\lambda_0$ and $\lambda_g$ is as follows:

$$\lambda_g = \lambda_0 / \sqrt{\in_{\mathit{eff}}} \quad (2)$$

As can be seen from formula (2), the guided wavelength may be significantly smaller than the freespace wavelength. Taking, for example, an $\in_{\mathit{eff}}$ of about 80, the guided wavelength is almost one order of magnitude smaller than the freespace wavelength. Since the interstitial fluid probe volume 10 is a fluid composed of significant amount of water, it can be modelled as an aqueous glucose solution for a first approximation, in case the interstitial fluid parameter is a glucose concentration. The permittivity $\in_{r2}$ can be described as a Debye model that is a function of frequency ω and glucose concentration χ as follows $$\varepsilon_{r2}(\omega, \chi) = \varepsilon_\infty(\chi) + \frac{\varepsilon_{\mathit{stat}}(\chi) - \varepsilon_\infty(\chi)}{1 + j\omega\tau(\chi)} \quad (3)$$

In formula (3), $\in_\infty$, $\in_{\mathit{state}}$ and τ are static and infinity permittivity and the relaxation time, respectively. In consideration of the relation between the propagation characteristics and the effective permittivity of the waveguide unit 190, the attenuation constant and the wave number of the waveguide unit 190 are also a function of the glucose concentration within the interstitial fluid probe volume 10. Assuming the system of the waveguide unit 190 and the aqueous solution of the interstitial fluid probe volume 10 as a linear system, the propagation characteristics can be measured with an M-sequence system, which will be described below with regard to FIGS. 7A to 7C, and therefore the glucose concentration within the interstitial fluid probe volume 10.

Figure 6A:
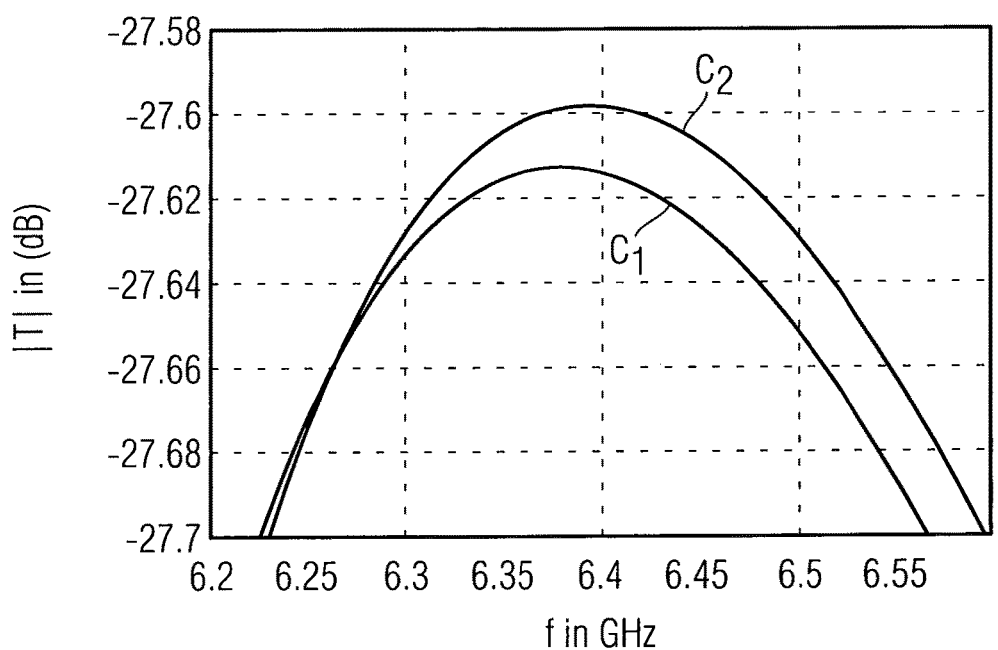
FIG. 6A is a diagram illustrating a frequency shift of a maximum of a forward transmission factor vs. electromagnetic wave frequency characteristics at different interstitial fluid glucose concentrations.
Figure 6B:
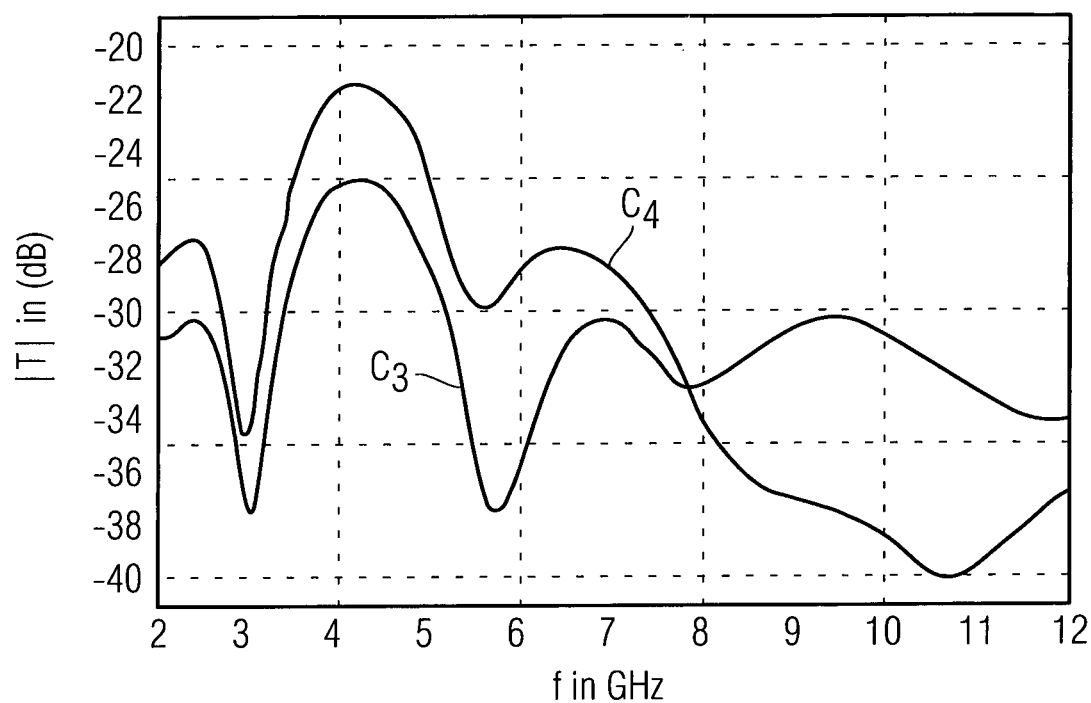
FIG. 6B is a diagram showing a forward transmission factor vs. electromagnetic wave frequency characteristics at different interstitial fluid glucose concentrations in a frequency band between 2 GHz and 12 GHz.

As illustrated by the diagram of FIG. 6A, the forward transmission factor T of the waveguide unit 190 has a different characteristics vs. the electromagnetic wave frequency at different glucose concentrations $C_1$ and $C_2$ within the interstitial fluid probe volume 10, wherein $C_2 > C_1$. As can be seen in FIG. 6A, a local maximum of the forward transmission factor T vs. electromagnetic wave frequency characteristics is shifted in dependence on the glucose concentration. Thus, the frequency shift in dependence on the glucose concentration may be used to determine the glucose concentration in the interstitial fluid probe volume 10. Furthermore, the complete spectrum may be analysed to assign to each glucose concentration such as $C_3$ and $C_4$ in the interstitial fluid probe volume 10 a respective spectrum, e.g. by a learning algorithm or a reference database. Herein, raw data of the measured spectra of the interstitial fluid probe volume 10 at different values of the interstitial fluid parameter may be transmitted from the transceiver unit 140 to the external reader 200, wherein the interstitial fluid parameter is measured invasively, e.g. by blood withdrawal. The respective spectra are then correlated with the invasively measured interstitial fluid parameter in a learning phase of the implanted electromagnetic wave sensor 100. The shift of different maxima of the electromagnetic wave transmission spectrum may occur in both directions, thus a characteristic signature may be determined, which reduces the influence of parameters being different from the interstitial fluid parameter of interest. The measured spectra may be different for different implantation environments, however the differential behaviour of the spectra in dependence of the interstitial fluid parameter ensures a definite detection of the interstitial fluid parameter.

The frequency range of the electromagnetic wave sensor 100 may be the microwave range between 300 MHz and 30 GHz, and/or the millimeter wave range between 30 GHz to 300 GHz, and/or the sub-millimeter range between 300 GHz to 3 THz. For providing the possibility of a broadband analysis of the transmission and/or reflection spectra of the emitted electromagnetic waves, the electromagnetic wave transmitter unit 120, the waveguide unit 190 and the electromagnetic wave receiver unit 130 may be adapted for broadband emission, broadband guidance and broadband reception. Spectra of interest are parts of the electromagnetic spectrum, in which the interstitial fluid transmission/reflection characteristic is strongly influenced by the presence of the interstitial fluid parameter such as glucose. Interesting frequency ranges for glucose are frequencies around 5.6 GHz or around 20 GHz. Thus, according to an embodiment, the electromagnetic wave transmitter unit 120, may be configured to emit electromagnetic wave signals in a frequency range between 1 GHz and 25 GHz. Further interesting frequency ranges may be frequencies between 70 GHz and 80 GHz, frequencies around 160 GHz, or frequencies up to 300 GHz. Thus, according to another embodiment, the electromagnetic wave transmitter unit 120 may be configured to emit electromagnetic wave signals in a frequency range between 300 MHz and 300 GHz, or between 1 GHz and 200 GHz, or between 1 GHz and 100 GHz, or between 1 GHz and 50 GHz. The electromagnetic wave transmitter unit 120 may be adapted to emit microwaves in a complete range of 300 MHz to 30 GHz. According to an embodiment, the bandwidth of the emitted electromagnetic wave signal of the electromagnetic wave transmitter unit 120 may be 500 GHz, or 200 GHz, or 100 GHz, or 50 GHz, or 30 GHz. According to an embodiment, the spectrum analysis of the interstitial fluid may be performed by sequentially switching harmonic frequencies to be emitted in a fringe field by the waveguide unit 190. To achieve a broadband analysis, at least two units comprising one electromagnetic wave transmitter unit 120, one waveguide unit 190 and one electromagnetic wave receiver unit 130 may be provided, which are specifically adapted for a certain frequency range, wherein all units cover a broad frequency range to be analysed.

Figure 7A:
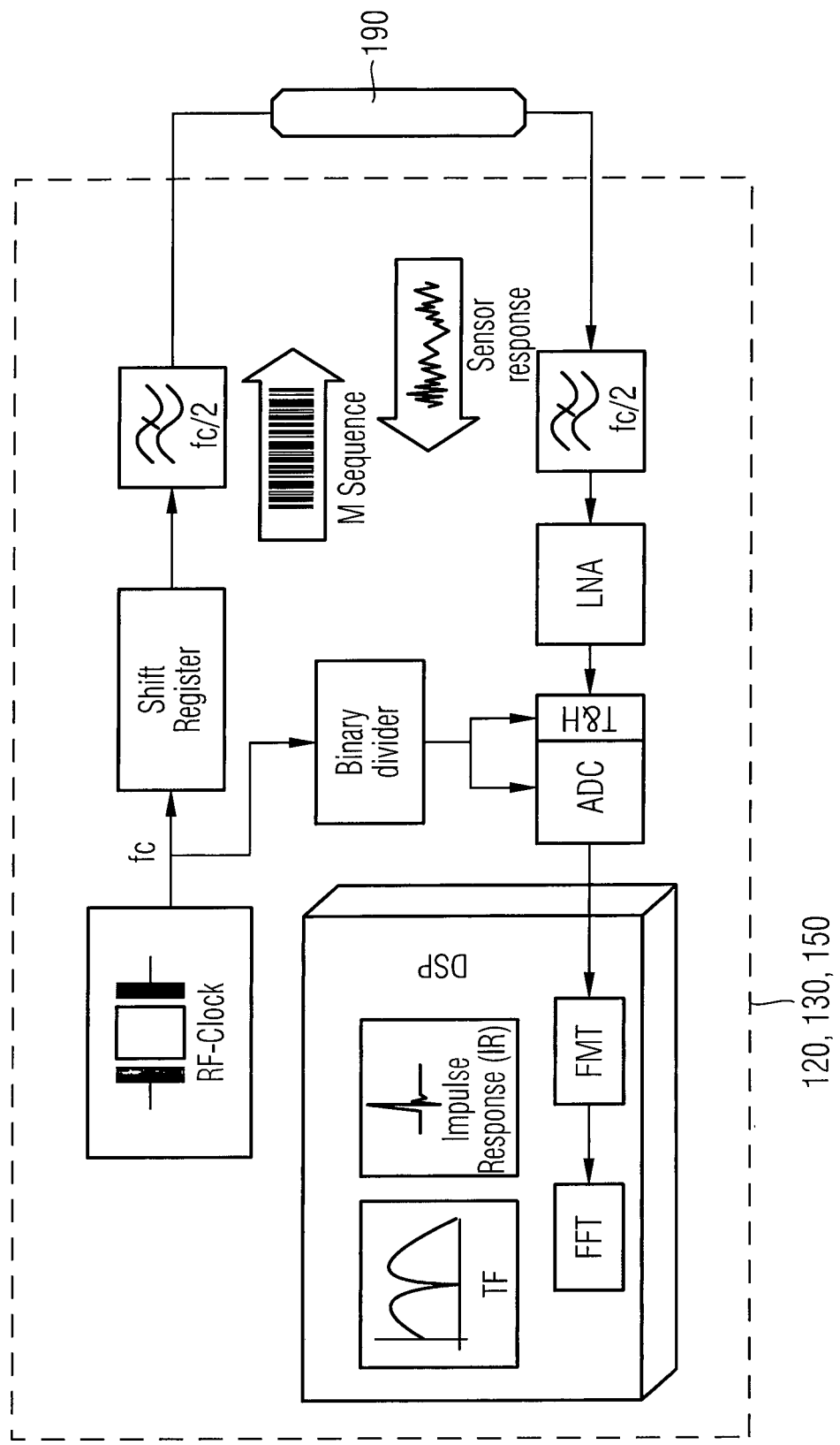
FIG. 7A is a schematic block diagram illustrating an ultra-wideband impedance spectrometer setup in a transmission mode of the electromagnetic wave sensor according to an embodiment.
Figure 7B:
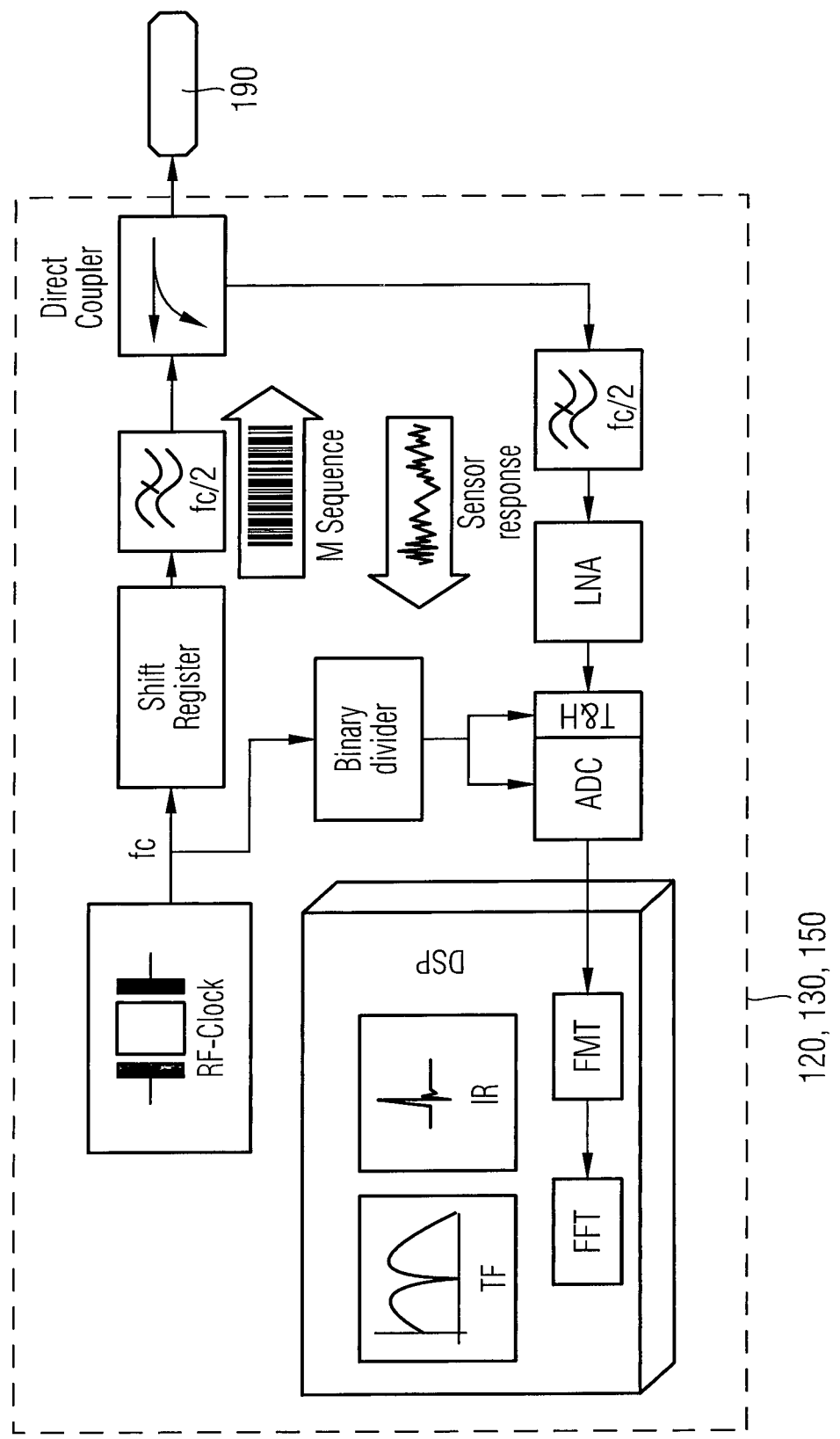
FIG. 7B is a schematic block diagram illustrating an ultra-wideband impedance spectrometer setup in a reflection mode of the electromagnetic wave sensor according to an embodiment.

The spectrum of the forward transmission factor T vs. the electromagnetic wave frequency may be determined by an ultra-wideband impedance spectrometer as shown in FIG. 7A to FIG. 7C.

According to random noise theory, the cross-correlation of an input with an output of a linear time-invariant system (LTI) under white noise excitation is proportional to a system impulse response h. From signal processing theory, the impulse response of the system in the time domain is equivalent to the transfer function of the system in the frequency domain. Therefore, the Fourier transform of the impulse response gives the transfer function (TF) of the LTI system. The random noise may be replaced with a maximum length sequence (M-sequence). Maximum length sequences are periodic sequences of integers. In the case of binary sequences, the integers are restricted to having two values only, say +1 and −1. They are generated by n-stage shift registers and the period length L is $$L = 2^n - 1 \quad (4)$$

The M-sequences have two characteristics that are important. The first one is that the Fourier transform (FT) has the same magnitude for all frequency components (except the dc component). Thus, their power spectrum is like that of a single impulse, namely independent of frequency. It is only necessary to cross-correlate the output response of the system Y with the same M-sequence that is used for exciting the system to obtain the desired system impulse response. The normalized impulse response of the system is given by $$h = MY/(L+1) \quad (5)$$

In formula (5), the vectors h and Y are the vectors of L elements corresponding to the impulse response and the output response of the LTI system. M is an L×L matrix containing the right circularly delayed version of the sequence M with a period equal to L times the clock period. The computation MY can be performed efficiently by using special techniques developed in Hadamard spectroscopy. When the Hadamard transformation is applied to an M sequence, it is called fast M-sequence transformation (FMT). It provides an efficient way to derive the cross-correlation function between the M-sequence excitation signal and the output response of the system, because it consists of only additions and substractions. The second property is concerned with the periodicity of the M-sequences. Thanks to the periodicity of the M-sequences, it is possible to subsample the output signal of the system in order to use low cost analogue to digital converters.

The properties of the M-sequence are useful to characterize linear systems and can be used in the area of the electromagnetic wave and millimetre wavelength signals to construct an ultra-wideband impedance spectrometer.

A schematic diagram of a measurement system comprising the electromagnetic wave transmitter unit 120, the electromagnetic wave receiver unit 130, the processor unit 150, and the waveguide unit 190 is illustrated in FIG. 7A. The M-sequence is generated by a fast n-stage shift register with an appropriate feedback, which is driven by an RF clock frequency $f_c$. Since nearly 80% of the signal energy is concentrated from DC to $f_c/2$, the M-sequence signal has to be low pass filtered to $f_c/2$. The filtered M-sequence is applied to the linear time invariant system to be characterized, which may be the waveguide unit 190 having an electromagnetic wave fringe field being in contact with the interstitial fluid probe volume 10. After low pass filtering and amplification by means of a Low-Noise Amplifier LNA, the response of the system in the continuous time domain is sampled into digital form by an A/D converter ADC. The clock rate of the M-sequence will be divided by a frequency binary divider in order to drive the A/D converter ADC and a track and hold unit T&H in a subsampling mode. Within a digital signal processor DSP, the sampled response is converted into the impulse response using the FMT. Finally, a fast fourier transform (FFT) gives the transfer function (TF) of the system in the frequency domain.

With the systems comprising the electromagnetic wave transmitter unit 120, the electromagnetic wave receiver unit 130, the processor unit 150, and the waveguide unit 190 as shown in FIGS. 7A to 7C, it is possible to measure the response in transmission and in reflection of the waveguide unit 190. Herein, FIG. 7A shows a system comprising the electromagnetic wave transmitter unit 120, the electromagnetic wave receiver unit 130, the processor unit 150, and the waveguide unit 190 for transmission measurement. FIG. 7B shows a measurement system comprising the electromagnetic wave transmitter unit 120, the electromagnetic wave receiver unit 130, the processor unit 150, and the waveguide unit 190 for reflection. In comparison with the setup for measurements in transmission, the system to measure the response of this waveguide unit 190 in reflection as shown in FIG. 7B is equipped with a directional coupler that enables the measurement of the electromagnetic waves that are reflected in the electromagnetic wave guide unit 190 due to the impedance mismatch depending on composition of the interstitial fluid probe volume 10.

As shown in FIG. 7C, a system comprising the electromagnetic wave transmitter unit 120, the electromagnetic wave receiver unit 130, the processor unit 150, and the waveguide unit 190 may also be configured to measure a response of the waveguide unit 190 in transmission and in reflection. Herein, the system additionally includes a second measurement path to record a reference signal. The reference signal can be used to calibrate changes in the sender power and in the phase. To save energy, only one additional measurement path was added. That means that it is only possible to measure either the reflection response or the transmission response at one time.

By means of the systems comprising the electromagnetic wave transmitter unit 120, the electromagnetic wave receiver unit 130, the processor unit 150, and the waveguide unit 190 as described above with regard to FIGS. 7A to 7C, a transmission or reflection spectrum of the interstitial fluid probe volume 10 of the waveguide unit 190 having a fringe field penetrating the interstitial fluid probe volume 10 may be measured. As shown with regard to FIGS. 6A and 6B, the measured spectrum may be used to determine the glucose concentration within the interstitial fluid probe volume 10.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electromagnetic wave sensor for determining an interstitial fluid parameter in vivo, comprising:
    an implantable housing; and
    a sensor component hermetically encapsulated within the implantable housing, the sensor component comprising an electromagnetic wave transmitter unit configured to emit an electromagnetic wave signal in a frequency range between 3 GHz and 3 THz penetrating the implantable housing and penetrating an interstitial fluid probe volume, an electromagnetic wave receiver unit configured to receive the electromagnetic wave signal modified by the interstitial fluid probe volume, and a transceiver unit configured to transmit radio frequency signals related to the electromagnetic wave signal modified by the interstitial fluid probe volume,
    wherein the sensor component further comprises a waveguide unit arranged within the implantable housing and coupled to the electromagnetic wave transmitter unit and the electromagnetic wave receiver unit,
    wherein the waveguide unit is a dielectrically loaded waveguide or transmission line that only partially contains the electromagnetic wave signal and from which a fringe field of the electromagnetic wave signal extends into the interstitial fluid probe volume.

2. The electromagnetic wave sensor of claim 1, wherein the implantable housing is made of a non-metallic biocompatible material suitable for long-term implantation in a human or animal.

3. The electromagnetic wave sensor of claim 1, wherein the implantable housing comprises means for fixing the implantable housing within a surrounding subcutaneous tissue of a human or other animal.

4. The electromagnetic wave sensor of claim 1, wherein the interstitial fluid parameter is a glucose concentration within the interstitial fluid probe volume.

5. The electromagnetic wave sensor of claim 1, wherein the electromagnetic wave transmitter unit is configured to emit electromagnetic wave signals in a frequency range between 5.6 GHz and 20 GHz.

6. The electromagnetic wave sensor of claim 1, wherein the waveguide unit is directly connected to the electromagnetic wave receiver unit, and wherein a phase of the emitted electromagnetic wave signal by the interstitial fluid probe volume occurs in the waveguide.

7. The electromagnetic wave sensor of claim 1, wherein the electromagnetic wave transmitter unit and the electromagnetic wave receiver unit are arranged at opposite ends of the waveguide unit.

8. The electromagnetic wave sensor of claim 1, wherein the electromagnetic wave transmitter unit and the electromagnetic wave receiver unit are arranged at a same end of the waveguide unit.

9. The electromagnetic wave sensor of claim 1, wherein a length of the waveguide unit is a quarter or half of a maximum guided wavelength of the electromagnetic wave signal.

10. The electromagnetic wave sensor of claim 1, wherein the waveguide unit is a micro strip line.

11. The electromagnetic wave sensor of claim 1, wherein the sensor component is integrated in a monolithic circuit.

12. The electromagnetic wave sensor of claim 1, wherein the sensor component further comprises a processor unit configured to process parameters of the emitted electromagnetic wave signal received from the electromagnetic wave transmitter unit and parameters of the electromagnetic wave signal modified by the interstitial fluid probe volume received from the electromagnetic wave receiver unit.

13. The electromagnetic wave sensor of claim 1, wherein the sensor component further comprises a memory unit configured to store measurement data or processed data.

14. The electromagnetic wave sensor of claim 1, wherein the transceiver unit is configured to receive update programs for adapting the operation of the transceiver unit and to transfer data to a cellular phone.

15. The electromagnetic wave sensor of claim 1, wherein the sensor component further comprises a temperature sensor configured to measure a temperature of the interstitial fluid probe volume.

16. The electromagnetic wave sensor of claim 1, wherein the sensor component further comprises an energy storage unit and an energy harvesting unit configured to harvest energy from an external power source.

17. The electromagnetic wave sensor of claim 16, wherein the sensor component further comprises an antenna unit connected to the transceiver unit and the energy harvesting unit.

18. A system for determining an interstitial fluid parameter in vivo, comprising:
    an electromagnetic wave sensor; and
    an external reader,
    wherein the electromagnetic wave sensor comprises an implantable housing and a sensor component hermetically encapsulated within the implantable housing, the sensor component comprising an electromagnetic wave transmitter unit configured to emit an electromagnetic wave signal in a frequency range between 3 GHz and 3 THz penetrating the implantable housing and penetrating an interstitial fluid probe volume, an electromagnetic wave receiver unit configured to receive the emitted electromagnetic wave signal modified by the interstitial fluid probe volume, and a transceiver unit configured to communicate with the external reader, wherein the external reader is configured to transmit radio frequency energy powering the electromagnetic wave sensor and to receive radio frequency signals from the electromagnetic wave sensor related to the electromagnetic wave signal modified by the interstitial fluid probe volume, wherein the sensor component further comprises a processor unit configured to detect a phase shift to the emitted electromagnetic wave signal by the interstitial fluid probe volume.

19. The system of claim 18, wherein the external reader is one of a cellular phone, a personal computer, a tablet personal computer, or a bedside device.

20. The system of claim 18, wherein the external reader is a mobile device fixed to an armband or to a belt.

21. The electromagnetic wave sensor of claim 12, wherein the processor unit is configured to detect a frequency shift of at least one maximum of an electromagnetic wave transmission or an electromagnetic wave reflection by the interstitial fluid.

\* \* \* \* \*